United States Patent [19]
Krämer et al.

[11] Patent Number: 6,166,067
[45] Date of Patent: Dec. 26, 2000

[54] INHIBITORS OF CHOLESTEROL-BIOSYNTHESIS FOR REDUCING THE CHOLESTEROL CONTENT OF POULTRY EGGS

[75] Inventors: Klaus Krämer, Landau; Kai-Uwe Baldenius, Frankenthal; Peter Paul Hoppe, Wachenheim, all of Germany

[73] Assignee: BASF Aktiengesellschaft, Ludwigshafen, Germany

[21] Appl. No.: 09/362,062

[22] Filed: Jul. 28, 1999

[30] Foreign Application Priority Data

Aug. 7, 1998 [DE] Germany .......................... 198 35 850

[51] Int. Cl.⁷ ........................ A61K 31/355; A61K 31/22; A61K 31/12; A61K 31/045; A61K 31/01
[52] U.S. Cl. .......................... 514/458; 514/546; 514/690; 514/739; 514/762
[58] Field of Search ................................... 514/458, 546, 514/690, 739, 762

[56] References Cited

U.S. PATENT DOCUMENTS

| | | | |
|---|---|---|---|
| 4,603,142 | 7/1986 | Burger et al. ............................ | 514/456 |
| 5,217,992 | 6/1993 | Wright et al. ............................ | 514/458 |
| 5,296,508 | 3/1994 | Pearce ..................................... | 514/510 |
| 5,919,818 | 7/1999 | Lane et al. ............................... | 514/458 |

FOREIGN PATENT DOCUMENTS

| | | |
|---|---|---|
| 543417 | 5/1993 | European Pat. Off. . |

OTHER PUBLICATIONS

Elson, *Dietary Fats, Lipids, Hormones and Tumorigenesis*, 1996, 71–86.
Hood et al., *Poultry Science*, 57(1), 1978, 304–306.
Database Biosis, XP002122917 (Pearce et al., *J. Med. Chem.*, 37(4), 1994, 526–541).
Database FSTA, XP002122918 (Qureshi et al., *Nutrition Research*, 11(2/3), 1991, 159–168).
Database FSTA, XP002122919 (Sugiyama et al., *J. Nutritional Sci. and Vitaminology*, 38(4), 1992, 335–342).
Palca, Science 247, 1170–1171, 1990.
Morel, D. W. and Lin Y. C., Nutr. Biochem. 7, 495–506, 1996.
Holvoet, P. and Collen D., FASEB J. 8, 1279–1284, 1994.
Jha, P. et al., Ann. Int. Med., 123, 11, 860–872, 1995.
Poulter N., et al., Am. J. Clin. Nutr., 58: 66–9, 1993.
Dubois C. et al., Am. J. Clin. Nutr. 61, 325–333, 1995.
McIntosh G. H. et al., World Rev. Nutr. Diet 77, 89–108, 1995.
Qureshi, A. A. et al., J. Biol. Chem. 261, 10544–10550, 1986.
Hegstedt, M. and Kousik, C. S., Louisiana Agriculture 36, 2, 16–17, 1994.
Qureshi, N. and Qureshi, A. A., in: Packer, L. und Fuchs, J. (ed.), Vitamin E in Health and Disease. Marcel Dekker, New York, 1993, 247–267.
Lia et al., Am. J. Clin. Nutr. 62, 1245–1251, 1995.
Beyer, R. S. and Jensen, L. S., Poultry Sci. 72, 1339–1348, 1989.
Naber, E. C., Feedstuffs 62, 5, 48–52, 1990.
Gerken, M., Jahrbuch für Geflügelwirtschaft, Verlag Eugen Ulmer, Stuttgart, 1994, 138–143.
Grashorn, M. A., Feed Mix 3, 4, 28–31, 1995.
Elkin, R. G. and Rogler, J. C., J. Agric. Food Chem. 38, 1635–1641, 1990.
Elkin, R. G. et al., J. Agric. Food Chem. 41, 1094–1101, 1993.
Huggett, C. D. et al., Biochem. Soc. Trans. 21, 147, 1993.
Beyer, R. S. and Jensen, L. (Poultry Sci. 68, 1703–1706, 1993).
Elson, C., Am. Inst. Nutr. 1666–1672, 1995.
Yu, S. G. et al., Am. Chem. Soc. 42, 7, 1493–1498, 1994.
Yu, S. G. et al., Am. Inst. Nutr. 2763–2767, 1995.
Elson, C. E. and Yu, S. G., Am. Inst. Nutr., 607–614, 1994.
Fuhrmann et al., Biochem. Biophys. Res. Commun. 233, 658–662, 1997.
Bässler, K. H. et al., Vitamin–Lexikon für Ärzte, Apotheker und Ernährungswissen–schaftler, Gustav Fischer Verlag, 1992 (Table of Contents).
Qureshi, A. A. et al., Nutr. Rep. Int. 40, 5, 992–1001, 1989.

*Primary Examiner*—Kimberly Jordan
*Attorney, Agent, or Firm*—Keil & Weinkauf

[57] ABSTRACT

A recorded image frame is distorted on the printing plate when image information or image data from a computer is recorded in the form of band strips, with a plurality of image elements dotted on each widthwise dotted line of the band, on a printing plate wound over a drum. The present invention permits an undistorted recording on the printing plate by an arrangement which includes a printing plate wound around a drum in the form of a right circular cylinder, an exposing assembly to record image information in the form of a band strip on the printing plate by means of light beam, a moving mechanism to move the exposing assembly in relation to the drum in the direction of the drum axis—by one band width per revolution of the drum—and a circuit to generate and incline distortion offsetting signal in a sawtoothed pattern having the cycle synchronized with that of the rotation of the drum with the initial writing position on the band as starting point. Under this arrangement, this incline distortion offsetting signal is applied to the exposing assembly to gradually move the light beam in the direction opposite to the moving direction of moving mechanism—by one band width per revolution of the drum. This process is repeated until the whole printing image is recorded.

7 Claims, 2 Drawing Sheets

INHIBITORS OF CHOLESTEROL-BIOSYNTHESIS FOR REDUCING THE CHOLESTEROL CONTENT OF POULTRY EGGS

The use of inhibitors of cholesterol-biosynthesis for reducing the cholesterol content of poultry eggs The invention relates to the use of inhibitors of cholesterol-biosynthesis or hydroxymethylglutaryl (HMG)-coenzyme A (CoA) reductase for reducing the cholesterol content in poultry eggs, and to poultry feed compositions which comprise such inhibitors.

Cholesterol is an essential constituent of cell membranes in humans and animals and serves as starting material for the synthesis of steroid hormones and bile acids. Endogenous and exogenous cholesterol (dietary cholesterol) can be used in the same way for intermediary metabolic processes.

Hypercholesterolemia (>200 mg/dl) is, besides smoking, obesity, hypertension and hyperhomocysteinemia, a risk factor for coronary heart disease. The contribution of alimentary cholesterol to atherogenesis is still the subject of intense discussion. The effect of dietary cholesterol on plasma cholesterol is very variable. People without metabolic disorders scarcely react to an increase in the cholesterol intake. Part of the population (36% in the USA) responds to exogenous cholesterol with a pronounced rise in plasma cholesterol. In this population group there appears to be not only a higher absorption rate but also an impaired feedback mechanism for endogenous cholesterol synthesis. Epidemiological studies show that the risk of coronary heart disease is reduced by 2% when the plasma cholesterol level falls by 1% (Palca, Science 247, 1170–1171, 1990).

Cholesterol lowering measures comprise a reduction in the intake of fats, especially of saturated animal fats. The cholesterol limitation associated therewith takes second place. In addition, the proportion of mono- or polyunsaturated fatty acids in the diet should be increased, with the lipid-lowering effect of ω-3 fatty acids being particularly important (Deutsche Gesellschaft für Ernährung, Beratungsstandards, 1995).

According to recent findings, cholesterol per se does not appear to be the sole risk factor; on the contrary oxidized lipids, including oxycholesterols in the LDL fraction are included (Morel, D. W. and Lin Y. C., Nutr. Biochem. 7, 495–506, 1996). Increasing the intake of antioxidant substances, especially vitamin E, is therefore, according to several authors, a desirable preventive approach to avoiding ischemic disorders (Holvoet, P. and Collen D., FASEB J. 8, 1279–1284, 1994, Jha, P. et al., Ann. Int. Med., 123, 11, 860–872, 1995).

Despite the current differences in the ways of viewing dietary cholesterol, recommendations of national committees of experts, e.g. Deutsche Gesellschaft für Ernährung, US Nutrition Research Council, exist, also for the general population, limiting the daily cholesterol intake to 300 mg. Overall, the entire discussion about cholesterol has led to a high degree of insecurity among the population about the nutritional and health value of eggs. The consumption of eggs in Germany has therefore declined over 10 years from 280 to 218 per head of the population in 1994/95.

It is known from studies on humans that oat bran and rice bran, and barley, have a lipid-lowering effect (Poulter N., et al., Am. J. Clin. Nutr., 58–66–9, 1993; Dubois C. et al., Am. J. Clin. Nutr. 61, 325–333, 1995; McIntosh G. H. et al., World Rev. Nutr. Diet 77, 89–108, 1995). This effect was for a long time ascribed only to the content of soluble nonstarch polysaccharides (β-glucans) which reduce absorption of fats by adsorbing bile acids and increasing the viscosity in chyme. The cholesterol-lowering effect of these types of cereal is probably also attributable to their content of tocotrienols (mainly α-tocotrienol) (Qureshi, A. A. et al., J. Biol. Chem. 261, 23, 10544–10550, 1986; Hegstedt, M. and Kousik, C. S., Louisiana Agriculture 36, 2, 16–17, 1994; Qureshi, N. and Qureshi, A. A., in: Packer, L. und Fuchs, J. (ed.), Vitamin E in Health and Disease. Marcel Dekker, New York, 1993, 247–267; Lia et al., Am. J. Clin. Nutr. Diet 62, 1245–1251, 1995). Tocotrienols inhibit the key enzyme of cholesterol biosynthesis, β-hydroxy-β-methyl-glutaryl (HMG)-CoA reductase in the liver (post-transcriptional down-regulation). The most effective isomer identified in HepG2 cell cultures was γ-tocotrienol (about 30 times stronger than α-tocotrienol). There were no differences between the racemic (synthetic) and natural (chiral) forms. The effect of the nicotinate was most pronounced by comparison with the alcohol and acetate forms (U.S. Pat. No. 5,217,992).

Attempts to influence the cholesterol content of poultry eggs by dietary measures have had little success to date (Beyer, R. S. and Jensen, L. S., Poultry Sci. 72, 1339–1348, 1989; Naber, E. C., Feedstuffs 62, 5, 48–52, 1990; Gerken, M., Jahrbuch für Geflügelwirtschaft, Verlag Eugen Ulmer, Stuttgart, 1994, 138–143; Grashorn, M. A., Feed Mix 3, 4, 28–31, 1995). With synthetic HMG-CoA reductase inhibitors, called statins, however, there was a reduction of 15% (lovastatin) or 30% ((±)-(R*,R*)-3,4-dibromo-β,δ-dihydroxy-2-(4-fluorophenyl)-5-(1-methylethyl)-1H-pyrrole-1-heptanoic acid, Na salt) without influencing the poulty performance parameters, such as the egg output (Elkin, R. G. and Rogler, J. C., J. Agric. Food Chem. 38, 1635–1641, 1990; Elkin, R. G. et al., J. Agric. Food Chem. 41, 1094–1101, 1993). However, statins are synthetic drugs so that, when they are used for feeding, there is a risk of unwanted localization of synthetic residues in the egg. However, in another study, simvastatin had no effect on the cholesterol content in eggs (Huggett, C. D. et al., Biochem. Soc. Trans. 21, 147, 1993).

The reduction in cholesterol by tocotrienols in humans, broilers and hypercholesterolemic pigs was investigated in U.S. Pat. No. 5,217,992. No attempts to reduce cholesterol in poultry eggs were described. According to a study by Beyer, R. S. and Jensen, L. (Poultry Sci. 68, 1703–1706, 1993) α-tocotrienol has no effect at any rate on the cholesterol content in eggs. Laying hens depend on a minimum synthesis of cholesterol because cholesterol is required for synthesizing sex hormones. The estrogen level is accordingly particularly high in hens. Chicks also require a minimum cholesterol content of the yolk during embryonic development. It therefore cannot be precluded that a forced reduction in cholesterol will have adverse effects on the egg output of laying hens and/or embryonic development of the chicks.

A number of derivatives (vegetable terpenoids) of the mevalonate pathway (cholesterol biosynthesis), e. g. linalool, geraniol and d-limonene, but also β-ionone, have been shown in chemoprevention experiments in cell culture and on laboratory animals such as rats and mice to inhibit HMG-CoA reductase and, associated therewith, to inhibit tumors (Elson, C., Am. Inst. Nutr. 1666–1672, 1995; Yu, S. G. et al., Am. Chem. Soc. 42, 7, 1493–1498, 1994; Yu, S. G. et al., Am. Inst. Nutr. 2763–2767, 1995; Elson, C. E. and Yu, S. G., Am. Inst. Nutr., 607–614, 1994). The carotenoids lycopene and β-carotene also inhibit cholesterol synthesis in macrophages (Fuhrmann et al., Biochem. Biophys. Res. Commun. 233, 658–662, 1997). However, this publication does not propose a possible use of these compounds for reducing the cholesterol content in poultry eggs, nor has this been investigated to date.

It is an object of the present invention to find a novel way of reducing the cholesterol content in poultry eggs.

We have found that this object is achieved by using at least one inhibitor as additive to poultry feed, the inhibitor comprising an isoprenoid structural element. The compounds which are effectiv according to the invention are cholesterol-biosynthesis inhibitors in a general way. Since their effect can be explained by an inhibition of HMG-CoA reductase (without being bound to it) they shall be called HMG-CoA reductase inhibitors, within the context of the present invention.

For the purpose of the present invention, substances with an isoprenoid structural element are compounds which have a basic carbon skeleton constructed on the isoprenoid principle, that is to say are constructed from isoprene units, i.e. $C_5$ building blocks, or are derived therefrom. They also mean compounds which comprise at least a partial structure which is constructed on such an isoprenoid principle. This isoprenoid structural element is additionally characterized by the presence of at least one carbon-carbon double bond. Examples of isoprenoid structural elements are those derived from terpene (i.e. $C_{10}H_{16}$), sesquiterpene (i.e. $C_{15}H_{24}$) or tetraterpene ($C_{40}H_{64}$).

Examples of HMG-CoA reductase inhibitors which can be used according to the invention are tocotrienols and terpenoids. Preferred terpenoids are vegetable terpenoids, especially those with a terpene, sesquiterpene or tetraterpene structure or a structure derived therefrom. Particular mention should be made of inhibitors with the terpene or sesquiterpene structure, and especially compounds selected from ionones, linalools, farnesyls and perillyl alcohol.

Examples of tocotrienols which should be mentioned are α-, β-, γ- and δ-tocotrienol, the 4-oxo analogs thereof and the esters of these compounds.

Tocotrienols have the following general formula:

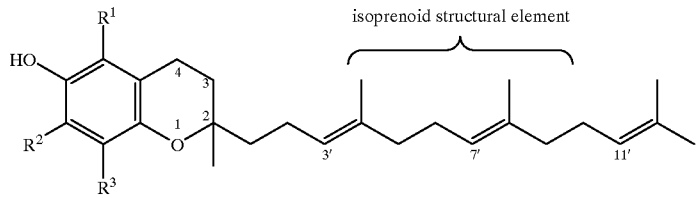

α-tocotrienol: $R^1=R^2=R^3=CH_3$
β-tocotrienol: $R^1=R^3=CH_3$, $R^2=H$
γ-tocotrienol: $R^1=H$, $R^2=R^3=CH_3$
δ-tocotrienol: $R^1=R^2=H$, $R^3=CH_3$ 4-Oxo analogs thereof have a keto group in position 4. An example thereof which may be mentioned is: 4-oxo-γ-tocotrienol. Suitable esters of the above tocotrienols are esterified via the 6-OH group for example with a mono- or dibasic, saturated or mono- or polyunsaturated $C_2$–$C_{22}$-carboxylic acid. Examples of suitable short-chain acids are $C_2$–$C_6$-carboxylic acids, e.g. formic acid, acetic acid, propionic acid or succinic acid. Examples of longer-chain acids are citric acid, palmitic acid, stearic acid, oleic acid, linoleic acid, α- and γ-linolenic acid, dihomo-γ-linolenic acid, arachidonic acid, eicosapentaenoic acid and docosahexaenoic acid. Also suitable are saturated or unsaturated heteroatom-containing carboxylic acids, e.g. α-lipoic acid or nicotinic acid.

Examples of terpenoids which can be used according to the invention and which should be particularly mentioned are vegetable terpenoids. The vegetable terpenoids are particularly selected from terpenes (compounds derived from a $C_{10}H_{16}$ structure), e.g. linalool, ionone and perillyl compounds; or sesquiterpenes (i.e. compounds derived from a $C_{15}H_{24}$ structure), e.g. farnesol compounds.

Ionones have the following general formula:

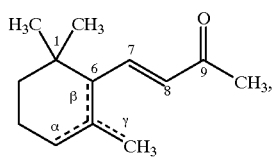

a distinction being made between α-, β- and γ-ionone depending on the position of the double bond.

Linalools which can be used according to the invention may be represented by the following formula:

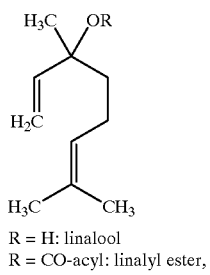

R = H: linalool
R = CO-acyl: linalyl ester, an example which may be mentioned of a linalyl ester being a linalyl $C_2$–$C_6$-carboxylic ester, e.g. linalyl acetate.

The perillyl alcohol which can likewise be used according to the invention has the following structural formula:

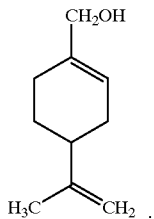

Farnesyls which can be used according to the invention and which should be mentioned are: farnesol of the formula

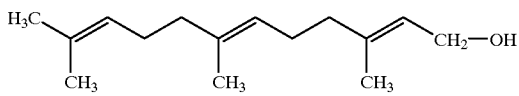

and the esters derived therefrom. Suitable esters which should be mentioned are esters of mono- or dibasic, saturated or mono- or polyunsaturated $C_2$–$C_{22}$-carboxylic acids. Examples of suitable short-chain acids are $C_2$–$C_6$-carboxylic acids such as formic acid, acetic acid, propionic acid or succinic acid. Examples of longer-chain acids are citric acid, palmitic acid, stearic acid, oleic acid, linoleic acid, α- and γ-linolenic acid, dihomo-γ-linolenic acid, arachidonic acid, eicosapentaenoic acid and docosahexaenoic acid. Also suitable are saturated or unsaturated heteroatom-containing carboxylic acids, e.g. α-lipoic acid or nicotinic acid.

Examples of tetraterpenes which can be used according to the invention are carotenoids. Those which should be particularly mentioned from the group of carotenoids are carotenes such as α-, β-, γ-, δ-, ε-, or ψ,ψ-carotene (lycopene) or all-trans-lycopene, but especially β-carotene and lycopene.

The inhibitors according to the invention of the type indicated above are administered mixed with conventional feedstuffs to the relevant poultry. The concentration of the inhibitor naturally varies depending on the particular active ingredient used, the type of poultry and the mode of feeding, but is approximately in the range from 5 to 10,000 mg/kg of feed. The active ingredient concentration which is optimal in each case can, however, be determined by the average skilled worker without difficulty. Typical ranges of contents (based on the total weight of the feed in kg) for some of the abovementioned inhibitors are:

Tocotrienols: 5–5000 mg/kg of feed
Oxo-tocotrienols: 5–5000 mg/kg of feed
Linalools: 10–5000 mg/kg of feed
β-Ionone: 10–5000 mg/kg of feed
Farnesol: 20–7500 mg/kg of feed
Perillyl alcohol: 5–7500 mg/kg of feed
Carotenoids: 5–7500 mg/kg of feed The present invention comprises the use of the abovementioned inhibitors in isomerically pure form, in optically pure form, as mixture of isomers or as mixture of stereoisomers or else as mixture of isomers and stereoisomers.

In a preferred embodiment, the inhibitors used are those which result both in a decrease in cholesterol in poultry eggs and in a decrease in triglycerides in poultry eggs and/or plasma. Examples which should be mentioned thereof are γ-tocotrienol esters such as γ-tocotrienol acetate.

The reductions in the cholesterol content of the yolk which can usually be achieved with inhibitors which can be used according to the invention are up to about 40%, preferably from about 10 to about 30%. Reductions in the triglyceride content in the yolk and in the plasma which can be observed according to the invention are in the region of about 30%, preferably about 10 to 20%. These values are usually achieved after feeding for a period of about 10 days.

The invention additionally relates to poultry feed compositions which comprise at least one of the HMG-CoA reductase inhibitors indicated above in combination with conventional feed components. Typical feed components which should be mentioned are: corn, barley, wheat, oats, rye, tritikale, sorghum, rice and brans, middlings brans, and meals of these types of cereals, soybeans, soybean products such as extracted soybean meal, oilseed rape, extracted rapeseed meal, cottonseed and extracted meal, sunflowers, extracted sunflower meal, linseeds, extracted linseed meal, oilseed expellers, broad beans, peas, gluten, gelatin, tapioca, yeasts, single cell protein, meat and bone meal, meat meal, blood meal, fish meal, salts, minerals, trace elements, vitamins, amino acids, feed fat, oils (soybean, rapeseed, sunflower etc).

BRIEF DESCRIPTION OF THE DRAWINGS

The present invention is now described in detail with reference to the appended figures. These show FIG. 1 a bar diagram of the cholesterol contents found in chicken egg yolk when the feed contained various HMG-CoA reductase inhibitors plus vitamin E and nicotinic acid. The assignment of the individual bars is as follows: 1: control; 2: vitamin E, 1000 mg/kg; 3: γ-tocotrienol acetate, 20 mg/kg; 4: γ-tocotrienol acetate, 500 mg/kg; 5: d-limonene, 5000 mg/kg; 6: nicotinic acid, 1500 mg/kg; and 7: nicotinic acid, 15,000 mg/kg (data in each case in mg of inhibitor per kg of feed). An arrow above a bar indicates a decrease (↓) or an increase (↑) in the cholesterol content at $p<0.05$.

EXAMPLE 1 a) Feed Formulation

Figure 1:
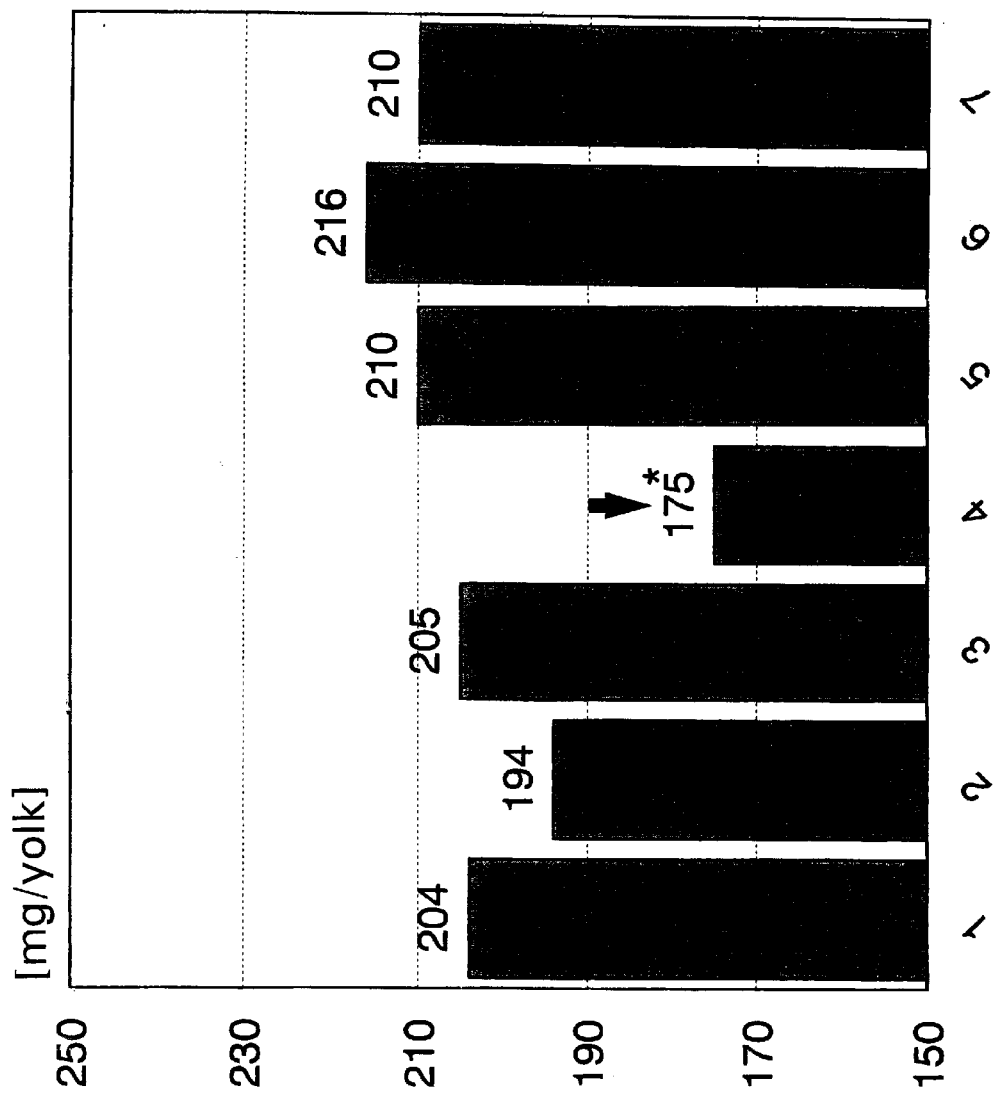

A trial feed in meal form based on corn and tapioca and having the composition indicated in Table 1 was produced. Barley, oats, wheat and rye were not used because these contain relevant amounts of tocotrienols. Soybean oil was used as source of fats and carrier of essential fatty acids, it, like corn oil and olive oil, containing no tocotrienol (cf. Qureshi & Qureshi, 1993, loc.cit.).

TABLE 1

| Composition and analyzed nutrient contents of the trial diet | |
|---|---|
| Composition | % |
| Corn | 48.000 |
| Tapioca | 16.000 |
| HP soybean meal | 18.000 |
| Starch | 2.000 |
| Wheat bran | 1.430 |
| Salt | 0.350 |
| Calcium carbonate | 7.900 |
| Cefkaphos (MCP)[1] | 1.300 |
| Vitamin PM[2] | 0.400 |
| Trace element PM | 0.020 |
| Choline chloride 70% | 0.120 |
| Soybean oil | 4.000 |
| Luprosil salt | 0.400 |
| Nutrient content | % |
| Water | 9.90 |
| Crude protein | 14.10 |
| Crude fat | 7.30 |
| Crude fiber | 3.00 |
| Crude ash | 12.30 |
| Total sugars | 3.00 |
| Crude starch | 41.70 |
| Sodium | 0.15 |

TABLE 1-continued

Composition and analyzed nutrient contents of the trial diet

| | |
|---|---|
| Calcium | 3.79 |
| Phosphorus | 0.61 |
| ME (MJ/kg)[3] | 12.00 |

[1]Cefkaphos (MCP) = monocalcium phosphate
[2]PM = premix
[3]ME = metabolizable energy b) Trial Protocol The investigated active ingredients were added in 2 dosages to a feed formulation as shown in Table 1, with the exception of vitamin E (all-rac-α-tocopheryl acetate) which was used only in a dosage of 1000 mg/kg (cf. Table 2).

TABLE 2

Trial protocol 1

| Treatment No. | Active ingredient | Dosage in the feed [mg/kg] |
|---|---|---|
| 1 | — | — |
| 2 | (all-rac-α-Tocopheryl acetate) | 1000[a] |
| 3 | γ-Tocotrienol acetate, synth. | 20[a] |
| 4 | γ-Tocotrienol acetate, synth. | 500 |
| 5 | d-Limonene | 5000[b] |
| 6 | d-Limonene | 50000[b] |
| 7 | Nicotinic acid | 1500[c] |
| 8 | Nicotinic acid | 15000 |

[a]Effective dosage according to U.S. Pat. No. 5,217,992
[b]Based on chemopreventive effect on addition of 0.5% to the diet (Elson and Yu, 1994, loc.cit.)
[c]Dosages of 150–300 X RDA (recommended dietary allowance) are effective in humans (Bässler et al., 1992, loc.cit.)

Nicotinic acid and vitamin E (all-rac-α-tocopheryl acetate) were used in addition to the HMG-CoA reductase inhibitors. The cholesterol-lowering effect of high nicotinic acid doses has been reported for a long time in the literature (Bässler, K. H. et al., Vitamin-Lexikon für Ärzte, Apotheker und Ernährungswissenschaftler, Gustav Fischer Verlag, 1992). In broilers, a stimulation of HMG-CoA reductase was observed on vitamin E supplementation, and there was an increase in plasma cholesterol when cholesterol was fed at the same time (Qureshi, A. A. et al., Nutr. Rep. Int. 40, 5, 992–1001, 1989). It was intended in this trial to investigate this effect in laying hens.

At the start of the trial, the laying hens (Lohmann Selected Leghorn) had been laying for 28 weeks. One treatment group consisted of 10 hens. The birds were initially fed with the various active ingredients for 4 weeks. The eggs were then collected for the analyses. 3 independent yolk pools were formed from 6 eggs in each case and were deep-frozen until analyzed. Total cholesterol and triglycerides in the yolk were analyzed by enzymatic methods. The analyses were carried out as stated in the handbook "Veterinärmedizinische Laboruntersuchungen für die Diagnose und Verlaufskontrolle" (1985), 3rd edition, published by Boehringer Mannheim GmbH, Mannheim.

For the cholesterol determination, the cholesterol esters were cleaved to cholesterol and fatty acid by the action of cholesterol esterase. Free cholesterol is converted by atmospheric oxygen with the involvement of cholesterol oxidase into $\Delta^4$-cholestenone and hydrogen peroxide. The resulting hydrogen peroxide forms with 4-aminophenazone and phenol through the catalytic action of peroxidase a red dye whose intensity of color is directly proportional to the cholesterol concentration and can be measured at 500 to 550 nm.

The triglycerides are determined enzymatically via their glycerol content. The triglycerides are cleaved enzymatically by the enzymes lipase and esterase. The resulting glycerol is phosphorylated by ATP to glycerol 3-phosphate in the reaction catalyzed by glycerol kinase GK.

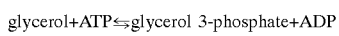
glycerol+ATP⇌glycerol 3-phosphate+ADP

The resulting ADP is converted by pyruvate kinase (PK) with phosphoenolpyruvate (PEP) back into ATP, with formation of pyruvate.

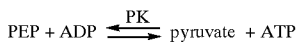
PEP + ADP $\xrightleftharpoons{PK}$ pyruvate + ATP

Pyruvate is hydrogenated to lactate by lactate dehydrogenase (LDH) with NADH, the NADH being oxidized to NAD.

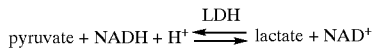
pyruvate + NADH + H⁺ $\xrightleftharpoons{LDH}$ lactate + NAD⁺

The amount of NADH consumed during the reaction is equivalent to the amount of glycerol. NADH is the measured variable and can easily be determined from its absorption at Hg 366 nm, Hg 334 nm or 340 nm.

Tocopherols and tocotrienols in the yolk pools were determined by HPLC. To do this, the sample is hydrolyzed in aqueous alcoholic medium and extracted several times with diethyl ether. Quantification takes place by comparison with external standards.

Stationary phase: Spherisorb CN 5 μm, 250×4 mm
Mobile phase: n-Hexane with 0.25% i-propanol
Flow rate: 2 ml/min
Fluorescence detection: 292 nm (extinction) 326 nm (emission)
UV/VIS: 326 nm.
Typical retention times are for:

| | |
|---|---|
| α-Tocopherol | 3.74 min |
| β-Tocopherol | 12.15 min |
| γ-Tocopherol | 12.93 min |
| β-Tocotrienol | 14.22 min |
| γ-Tocotrienol | 16.49 min |

At the end of the trial, raw and boiled eggs were subjected to an odor test.

The data were subjected to analysis of variance, and differences between means were ranged by the Duncan test.

c) Results

The odor test revealed no differences from the control.

Figure 2:
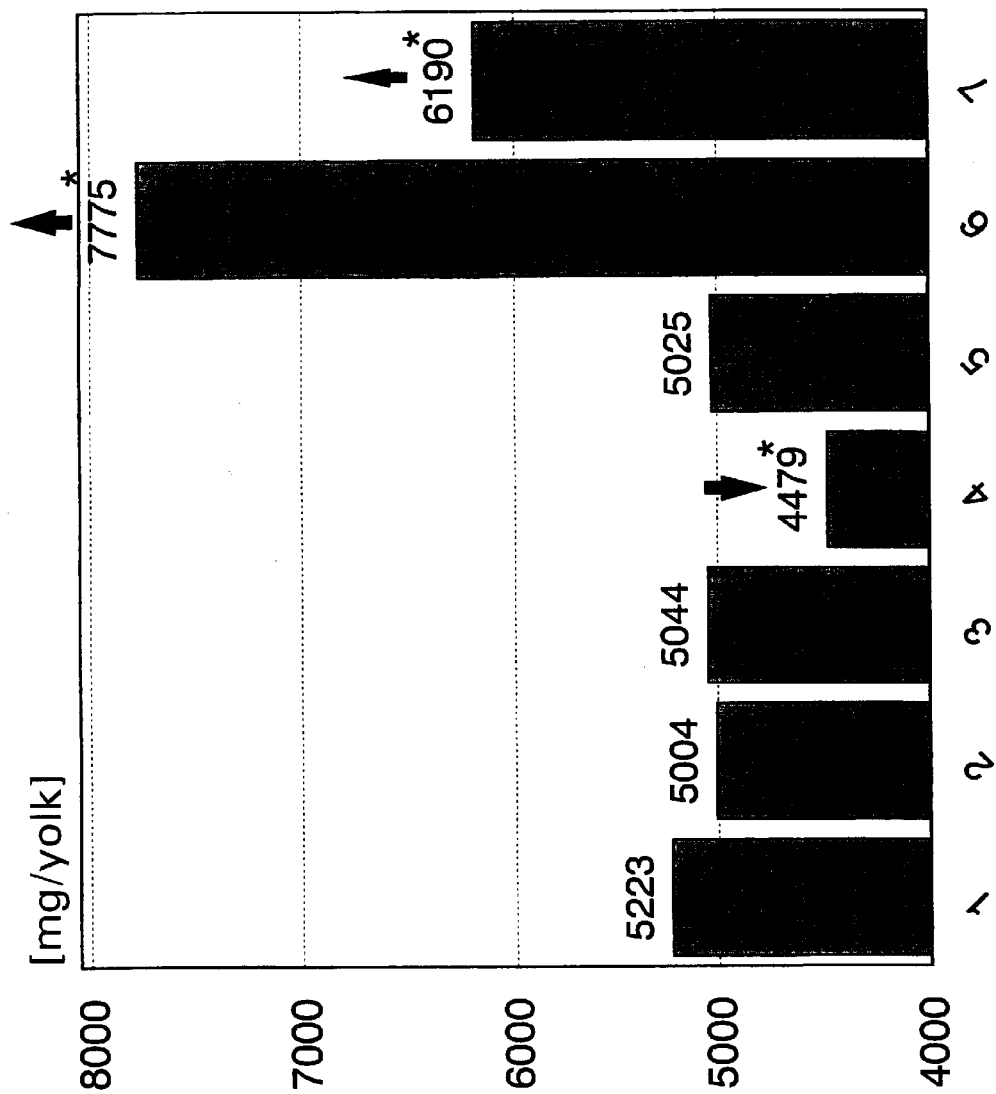
FIG. 2 a bar diagram of the triglyceride contents found in egg when the feed contained HMG-CoA reductase inhibitors, vitamin E and nicotinic acid. The assignment of the bars corresponds to FIG. 1.

The cholesterol and triglyceride contents found are shown in FIGS. 1 and 2. Since there were no significant differences between the yolk weights, the stated contents are based on the complete yolk. There were significant reductions of 15% in cholesterol and triglycerides in the yolk with γ-tocotrienol acetate, 500 mg/kg. The low tocotrienol dosage and vitamin E (all-rac-α-tocopheryl acetate) had no effect on these parameters. The triglyceride content was significantly increased by both nicotinic acid dosages.

The following Table 3 shows the tocopherol and tocotrienol contents in yolks with treatments 1, 2, 3 and 4.

Table 3: Tocopherol and tocotrienol contents in yolks on feeding with tocopheryl acetate and tocotrienol acetate

| Treatment | Active ingredient | Dosage in the feed [mg/kg] | α-Tocopherol | γ-Tocopherol | δ-Tocopherol [in each case μg/yolk] | α-Tocotrienol | δ-Tocotrienol |
|---|---|---|---|---|---|---|---|
| 1 | Control | 0 | 481 | 399 | 66 | 0 | 0 |
| 2 | all rac-α-tocopheryl acetate | 1000 | 23064 | 188 | 36 | 227 | 0 |
| 3 | R,S-γ-tocotrienol acetate | 20 | 545 | 393 | 57 | 0 | 0 |
| 4 | R,S-γ-Tocotrienol acetate | 500 | 433 | 425 | 59 | 0 | 366 |

These are the values found after hydrolysis. The α-tocopherol content in yolk rose from 0.48 mg in the control group to 23 mg with vitamin E (all-rac-α-tocopheryl acetate, 1000 mg/kg). This corresponds to a transfer rate of about 21%, which agrees well with literature values (Sünder, A. et al., Proc. Soc. Nutr. Physiol. 6, 147, 1997). In addition, the high α-tocopherol dosage caused a reduction in γ-tocopherol in the yolk. This finding is also known from the literature. There was surprisingly scarcely any accumulation of γ-tocotrienol in the yolk. Only at the high dosage was it possible to detect 366 μg of γ-tocotrienol in the yolk. The transfer rate into yolk was accordingly only about 0.008%.

EXAMPLE 2

Another feeding experiment was carried out in analogy to Example 1. In this case the intention was to test not only α- and δ-tocotrienol but also a tocotrienol precursor (4-oxo-γ-tocotrienol) and other terpenoids such as farnesyl acetate, perillyl alcohol, linalool and β-ionone, in laying hens.

a) Feed Formulation

Corn/tapioca/soybean (cf. Example 1)+150 ppm ethoxyquin (antioxidant)

Linoleic acid content adjusted to 1% with soybean oil

Vitamin E addition according to NRC (Nutrition Research Council/USA) (1994): 5 ppm all-rac-α-tocopheryl acetate b) Trial Protocol The trial protocol corresponds to that in Example 1 but with the following amendments:

The number of birds comprised 8 hens per treatment.

4 birds in each case from the control and the high dosages were sacrificed at the end of the trial. After taking blood to obtain plasma, the birds were completely exsanguinated. The liver was then removed and deep frozen until analyzed.

Triglyceride and cholesterol were determined in 4 independent yolk pools(each from 6 eggs) and plasma.

In addition, α-, δ- and 4-oxo-γ-tocotrienol in yolk and liver (treatments 1 to 7) were determined.

The trial protocol is depicted in Table 4 below:

TABLE 4

Trial protocol 2

| Treatment | Substance | Addition [mg/kg] |
|---|---|---|
| 1 | — | — |
| 2 | α-Tocotrienol | 50 |
| 3 | α-Tocotrienol | 500 |
| 4 | δ-Tocotrienol | 50 |
| 5 | δ-Tocotrienol | 500 |
| 6 | 4-Oxo-γ-tocotrienol | 50 |
| 7 | 4-Oxo-γ-tocotrienol | 500 |
| 8 | Linalool | 100 |
| 9 | Linalool | 1000 |
| 10 | β-Ionone | 100 |
| 11 | β-Ionone | 1000 |
| 12 | Farnesyl acetate | 750 |
| 13 | Farnesyl acetate | 7500 |
| 14 | Perillyl alcohol | 500 |
| 15 | Perillyl alcohol | 5000 | c) Results

The trial took place in accordance with the protocol and without defects. The treatments were found not to result in declines in the egg output or differences in the odor of the eggs.

The trial results for the cholesterol and triglyceride contents found are compiled in Table 5 below:

TABLE 5

| Active ingredient | Dosage in the feed mg/kg | Cholesterol Yolk [mg/g] | Cholesterol Plasma [mg/dl] | Triglycerides Yolk [mg/g] | Triglycerides Plasma [mg/dl] |
|---|---|---|---|---|---|
| — | — | 10.23 | 125.3 | 170.4 | 2496 |
| α-Tocotrienol | 50 | 9.85 | | 189.9 | |
| α-Tocotrienol | 500 | 9.45 | 130.3 | 195.1 | 4195 |
| δ-Tocotrienol | 50 | 9.25 | | 185.2 | |
| δ-Tocotrienoi | 500 | 9.23 | 163.0 | 163.9 | 2985 |
| 4-Oxo-γ-tocotrienol | 50 | 9.78 | | 188.3 | |
| 4-Oxo-γ-tocotrienol | 500 | 8.55 | 166.8 | 172.0 | 4336 |
| Linalool | 100 | 8.40 | | 187.5 | |
| Linalool | 1000 | 8.97 | 211.6 | 163.1 | 1907 |
| β-Ionone | 100 | 9.03 | | 190.7 | |
| β-Ionone | 1000 | 9.03 | 201.3 | 184.8 | 1954 |
| Farnesyl acetate | 750 | 10.15 | | 177.1 | |
| Farnesyl acetate | 7500 | 10.23 | 129.3 | 175.9 | 1929 |
| Perillyl alcohol | 500 | 9.55 | | 188.5 | |
| Perillyl alcohol | 5000 | 9.53 | 165.3 | 174.4 | 2197 |

The tocopherol and tocotrienol contents found in yolk and liver are summarized in Tables 6 and 7 below:

TABLE 6

Tocopherol and tocotrienol contents in yolk on feeding with α- and δ-tocotrienol and 4-oxo-γ-tocotrienol

| Active ingredient | Dosage in the feed [mg/kg] | α-Toco-pherol | β-Toco-pherol | γ-Toco-pherol | δ-Toco-pherol | α-Toco-trienol | γ-Toco-trienol | δ-Toco-trienol | 4-Oxo-γ-Tocotrienol |
|---|---|---|---|---|---|---|---|---|---|
| | | | | | [in each case μg/g] | | | | |
| — | — | 19.36 | 0.94 | 14.54 | 1.89 | 0.21 | 0.00 | 0.00 | 5.75 |
| α-Tocotrienol | 50 | 32.32 | 1.97 | 17.34 | 1.83 | 16.86 | 0.00 | 0.00 | 4.88 |
| α-Tocotrienol | 500 | 93.86 | 8.22 | 16.31 | 1.67 | 150.28 | 0.19 | 0.00 | 0.00 |
| δ-Tocotrienol | 50 | 25.89 | 0.93 | 16.97 | 1.56 | 0.75 | 0.26 | 0.63 | 2.01 |
| δ-Tocotrienol | 500 | 29.29 | 0.91 | 17.24 | 1.63 | 3.49 | 0.70 | 3.77 | 2.02 |
| 4-Oxo-γ-tocotrienol | 50 | 25.35 | 0.36 | 16.83 | 1.25 | 0.75 | 0.00 | 0.00 | 3.67 |
| 4-Oxo-γ-tocotrienol | 500 | 24.43 | 0.00 | 19.18 | 1.62 | 1.28 | 0.00 | 0.00 | 10.73 |

TABLE 7

Tocopherol and tocotrienol content in the liver of laying hens on feeding with α- and δ-tocotrienol and 4-oxo-γ-tocotrienol

| Active ingredient | Dosage in the feed [mg/kg] | α-Toco-pherol | β-Toco-pherol | γ-Toco-pherol | δ-Toco-pherol | α-Toco-trienol | γ-Toco-trienol | δ-Toco-trienol | 4-Oxo-γ-Tocotrienol |
|---|---|---|---|---|---|---|---|---|---|
| | | | | | [in each case μg/g] | | | | |
| — | — | 2.73 | n. d. | 1.46 | n. d. | 0.66 | n. d. | n. d. | n. d. |
| α-Tocotrienol | 500 | 11.82 | 1.25 | 2.64 | n. d. | 11.06 | n. d. | n. d. | n. d. |
| δ-Tocotrienol | 500 | 4.37 | n. d. | 2.26 | n. d. | 0.92 | n. d. | n. d. | n. d. |
| 4-Oxo-γ-tocotrienol | 500 | 4.15 | n. d. | 3.10 | n. d. | 1.00 | n. d. | n. d. | n. d. |

The above trial results show that there was a surprising trend toward reduced cholesterol contents in yolk with α- and δ-tocotrienol and perillyl alcohol. Surprisingly, there was also a significant reduction of up to 18% in yolk cholesterol with 4-oxo-γ-tocotrienol in the high dosage(500 mg/kg) and both dosages of the terpenoids linalool and β-ionone. The treatments had no effect on the plasma cholesterol content. By contrast, the plasma triglyceride level was reduced by a maximum of 25% by β-ionone, farnesyl acetate and perillyl alcohol. The triglycerides in yolk rose slightly with most of the treatments.

There was an increase in α-tocopherol in yolk with the tocotrienol treatments. The reason for this is that the products used still contained small amounts of α-tocopherol. There was an effect on β-tocopherol only by the α-tocotrienol treatments. The most pronounced increase for tocotrienols in yolk was for the α form. Extrapolated to the complete yolk, the retention was 2.4 mg with 500 mg/kg of α-tocotrienol, resulting in a transfer rate of about 2.2% which is, however, below that of α-tocopherol.

Besides α- and γ-tocopherol, only α-tocotrienol was detectable in the birds' livers.

We claim:

1. A method for reducing the cholesterol content in poultry eggs and/or the triglyceride content in plasma which comprises administering to the poultry at least one terpenoid in an amount effective to reduce the cholesterol content in poultry eggs and/or the triglyceride content in plasma.

2. The method of claim 1, wherein the terpenoid is a vegetable terpenoid.

3. The method of claim 2, wherein the vegetable terpenoid is β-ionone.

4. The method of claim 2, wherein the vegetable terpenoid is selected from linalool and the ester thereof.

5. The method of claim 2, wherein the vegetable terpenoid is a farnesyl ester.

6. The method of claim 1, wherein the terpenoid is employed in isomerically pure form, optically pure form, as isomer mixture of stereoisomer mixture or as mixture of isomers and stereoisomers.

7. The method of claim 1, wherein the terpenoid is administered mixed with feed which contains the terpenoid in a concentration which reduces the cholesterol content of poultry eggs and/or the triglyceride content in plasma.

* * * * *

UNITED STATES PATENT AND TRADEMARK OFFICE
CERTIFICATE OF CORRECTION

PATENT NO.: 6,166,067

DATED: December 26, 2000

INVENTOR(S): KRAEMER et al.

It is certified that error appears in the above-identified patent and that said Letters Patent is hereby corrected as shown below:

On the title page:
Cancel the abstract printed with the patent, which is totally erroneous, and substitute:
--The invention relates to the use of at least one cholesterol biosynthesis inhibitor for reducing the cholesterol content in poultry eggs, the inhibitor comprising an isoprenoid structural element.--

Signed and Sealed this

First Day of May, 2001

Attest:

NICHOLAS P. GODICI

*Attesting Officer*  *Acting Director of the United States Patent and Trademark Office*